United States Patent [19]

Waters

[11] Patent Number: 4,952,498

[45] Date of Patent: Aug. 28, 1990

[54] METHOD AND APPARATUS FOR DETECTING MICROORGANISM ACTIVITY

[76] Inventor: John R. Waters, P.O. Box 271789, Tampa, Fla. 33688

[21] Appl. No.: 191,197

[22] Filed: May 6, 1988

[51] Int. Cl.⁵ .................. C12Q 1/04; C12M 1/34; C12M 1/24
[52] U.S. Cl. .................... 435/34; 435/291; 435/296; 435/807; 73/19.01; 73/52; 220/203; 206/569; 116/70; 116/270
[58] Field of Search .............. 435/34, 289, 290, 291, 435/296, 807, 316; 73/19, 52; 422/102; 436/148; 220/203, 205, 209; 206/569; 116/270, 70

[56] References Cited

U.S. PATENT DOCUMENTS

| | | | |
|---|---|---|---|
| 2,296,848 | 9/1942 | Gueffroy | 116/270 X |
| 2,321,293 | 6/1943 | Hassler | 177/311 |
| 2,875,135 | 2/1959 | Maddox, Jr. | 435/34 X |
| 3,241,514 | 3/1966 | Grimland | 116/270 |
| 3,556,044 | 1/1971 | Egresits | 116/270 |
| 3,667,281 | 6/1972 | Pfeifer | 73/37 |
| 3,780,693 | 12/1973 | Parr | 116/270 |
| 3,859,844 | 1/1975 | Hruby | 73/45 |
| 3,907,646 | 5/1975 | Wilkins et al. | 195/103.5 |
| 3,949,610 | 4/1976 | Pietsch | 116/270 X |
| 4,117,718 | 10/1978 | Hayward | 73/52 |
| 4,152,213 | 5/1979 | Ahnell | 195/103.5 |
| 4,221,134 | 9/1980 | Ekstrom, Jr. | 73/721 |
| 4,326,408 | 4/1982 | Kanoh | 73/49 |
| 4,327,574 | 5/1972 | Alberghini et al. | 73/19 |
| 4,543,831 | 10/1985 | Meyer | 73/705 |
| 4,547,668 | 10/1985 | Tsikos | 250/231 |
| 4,588,886 | 9/1986 | Snider | 250/227 |
| 4,620,093 | 10/1986 | Barkhoudarian et al. | 250/231 |
| 4,706,830 | 11/1987 | Wareing | 116/270 X |
| 4,729,337 | 3/1988 | Schopp | 116/270 X |

Primary Examiner—Esther M. Kepplinger
Assistant Examiner—Toni R. Scheiner
Attorney, Agent, or Firm—Walter C. Farley

[57] ABSTRACT

Gas-generating activity of microorganisms is detected by providing a vessel in which the microorganisms are incubated, the vessel having a cap with a membrane indicator therein. The membrane has a deformed region which is inflated to indicate the existence of an increase in pressure within the vessel as compared with ambient pressure. Visual or automatic monitoring of the inflated portion is disclosed.

2 Claims, 3 Drawing Sheets

METHOD AND APPARATUS FOR DETECTING MICROORGANISM ACTIVITY

This invention relates to the detection of microorganism growth in a sealed container by detecting changes of pressure within the container resulting from that growth.

BACKGROUND OF THE INVENTION

The detection of bacterial activity within a container as evidenced by an increase of pressure within the container is well known, particularly in the food industry wherein an increase of pressure in a food container often indicates that the level of bacterial activity is so great as to render the food unsafe. Several devices for detecting such a pressure change have been developed using mechanical, electrical and other sensing means. Some of these employ devices which must penetrate the container while others respond to movement of a wall of the container using optical or other sensing.

It is highly desirable to be able to detect activity within a vessel in a laboratory context for determining the approximate population of a specific microorganism. Devices for this general purpose have also been devised. It is important, first, to be sure that the interior of the vessel, once supplied with a sample of the substance to be tested, is isolated from the ambient atmosphere to prevent contamination of the substance and also to prevent contamination of laboratory workers by the substance. Thus, the known pressure-change detecting techniques which involve penetration of the testing vessel for measurement purposes are hard to use and impractical. Of the other known techniques, while they are undoubtedly suitable for the purposes for which they were developed, they are relatively insensitive to small differences of pressure between the inside and outside of the container. Thus, such systems lack adequate sensitivity and, in some cases, an inordinate amount of time would be required to incubate the substance being tested to the point at which a pressure change could be sensed.

SUMMARY OF THE INVENTION

Accordingly, an object of the present invention is to provide a method of forming a pressure sensor for detecting small changes in pressure caused by the activity of a microorganism sample.

A further object is to provide a method of testing a substance by detecting small changes in pressure created by microorganism activity while maintaining high levels of safety and minimizing sample contamination.

A still further object is to provide an apparatus capable of detecting small changes in pressure resulting from microorganism activity.

Briefly described, the invention includes a method of making a pressure sensor for detecting small changes in pressure caused by the activity of a microorganism sample comprising the steps of providing a vessel having substantially rigid walls in a selected range of pressures and temperatures and having an opening into the interior of the vessel, providing a closure for closing the opening into the vessel, the closure including a membrane, and deforming a central portion of the membrane to form a flaccid indicator region which is significantly more movable than the remainder of the closure by differences in pressure across the closure so that a difference in pressure in one direction causes the region to form an outwardly bulging dome whereby microorganism activity of a type which generates a gas within the vessel in the selected range of pressures and temperatures causes a differential pressure which is evidenced by the bulging dome.

In another aspect, the invention comprises a method of detecting the presence of microorganisms in a sample comprising the steps of providing a vessel having substantially rigid walls in a selected range of pressures and temperatures and having an opening into the interior of the vessel, providing a closure for closing the opening into the vessel, the closure including a membrane, deforming the central portion of the membrane to form a flaccid indicator region which is significantly more movable by differences in pressure across the closure than the remainder of the membrane so that a difference in pressure in one direction causes the region to form an outwardly bulging dome, securely fastening the closure across the opening to seal the vessel, placing a sample of material in the vessel, placing the vessel in an incubating chamber having a controllable temperature, and incubating the vessel for a selected interval of time at a temperature and pressure within the selected range, Whereby microorganism activity within the vessel of a type which generates a gas causes a difference in pressure between the inside and outside of the vessel which is evidenced by the bulging dome.

In yet another aspect, the invention comprises an apparatus for detecting gas-generating activity of a substance containing microorganisms comprising the combination of a substantially rigid vessel for receiving a substance the activity of which is to be detected, the vessel having an opening through a wall thereof, and a substantially inelastic, flexible membrane having a substantially undeformed peripheral portion and a deformed central portion, the central portion having a surface area after deformation which is significantly greater than its area before deformation, the central area being flaccid and easily movable by pressure differences across the membrane to a plurality of positions including that of a dome protruding in the direction of lower pressure. Means is provided for holding the membrane in a fixed position across the opening so that the central portion is spaced from the walls of the vessel and is free to move. Means for detecting a protruding dome is provided to indicate a pressure difference caused by activity of microorganisms in the substance.

BRIEF DESCRIPTION OF THE DRAWINGS

In order to impart full understanding of the manner in which these and other objects are attained in accordance with the invention, particularly advantageous embodiments thereof will be described with reference to the accompanying drawings, which form a part of this specification, and wherein.

DESCRIPTION OF THE PREFERRED EMBODIMENTS

Figure 1:
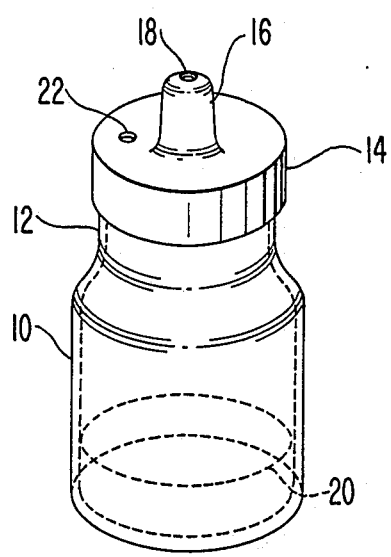
FIG. 1 is a perspective view of a vessel constructed in accordance with the invention for accomplishing the method thereof.

A vessel suitable for use with the method of the present invention is shown in FIG. 1, the vessel comprising a bottle 10 which is preferably made of glass so that it can be thoroughly sterilized, the bottle having a neck 12, the upper end of which is externally threaded. An internally threaded cap 14 engages the threads of the bottle, the cap having a central, dome-like protruding shell 16 with a vent hole 18 at its apex. The bottle is intended to receive a relatively small quantity of a substance indicated generally at 20 which is or contains microorganisms or which is to be tested for the purpose of determining the existence of microorganisms along with a culture medium. The substance 20 can be inserted into the bottle before the cap is applied or, alternatively, the cap can be provided with a sealable opening 22 through which the substance can be injected, as by a hypodermic needle, and then covered.

Figure 2:
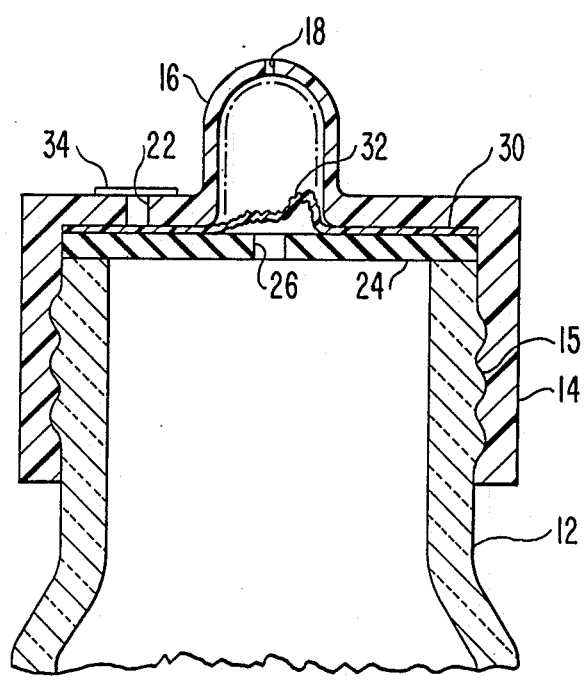
FIG. 2 is a partial side elevation, in section, of the vessel of FIG. 1.

The structure of the cap and bottle neck are more clearly seen in the sectional view of FIG. 2. As seen therein, the internal threads of cap 14 engage the external threads 15 on the neck 12 of the bottle. A sealing disk 24 is placed on the top surface of the neck 12 of the bottle, the disk being substantially rigid at the temperatures and pressures involved which would normally be in the general vicinity of 35°–37° C. and approximately atmospheric pressure, these conditions being commonly used for incubation because they are conducive to the growth of microorganisms. Disk 24 can conveniently be made of a polymeric material or ⅛ inch thick butyl rubber. Disk 24 has a central opening 26.

Between the inner surface of cap 14 and disk 24 is a liner 30 of a material which is flexible such as very thin rubber, vinyl material or Mylar film having a thickness on the order of 0.001–0.005 inches. Liner 30 forms a membrane which closes hole 22. The peripheral portion of membrane 30 is flat and is held by the cap and disk so as to be substantially rigid.

A generally circular central region thereof, however, can be deformed inelastically to create a thinner central region 32, the total area of which is greatly increased over the area of the circular portion which is deformed to create the region. This deformed area 32 is created by a thermoforming or molding process, usually at an elevated temperature, the actual temperature for deformation being selected on the basis of the material used. The objective of this deformation is to form a limp or flaccid pouch or thimble-like region which, normally, is easily movable to any position. It is particularly important to note, first, that the central region 32 is easily "inflatable" to occupy substantially the entire inner area of the inner surface of dome or shell 16, vent hole 18 being provided to prevent the creation of a counter pressure within the dome.

It is further important to note that this "inflation" can occur without any elastic deformation of the membrane material. The thinning and deformation of the material is accomplished beforehand, creating a very lightweight central deformable region which can be moved by very small pressure differentials between the interior of vessel 10 and the surrounding ambient atmosphere. It has been found that a material having a thickness of between about 0.001 and 0.003 inches can be inflated to occupy the interior of shell 16 by a pressure differential as small as 1.0 cm of water.

Some characteristics of this material should be clearly understood. The material should be very flexible but need not be elastic. Although those terms are sometimes loosely used as synonyms, the term "elastic" is more properly used to describe a material which can be deformed within limits and, when released, will return to its original shape and dimensions, or nearly so. Flexibility, on the other hand, implies that the material can be bent, folded and otherwise shaped, but not necessarily stretched elastically. As is well known, a common rubber balloon can be elastically inflated and will resume a size approximately its original size when vented. Inflation of that type requires considerable energy because energy is being stored during the elastic deformation. A material such as a lightweight plastic bag or finger cot, however, can be inelastically inflated from a collapsed condition with the expenditure of much less energy because there is no storage of energy in elastic deformation.

As previously indicated, the vessel is used by inserting a sample of the substance to be tested, such as a blood sample, into the vessel and then tightly fitting the cap, membrane and disk assembly onto the vessel neck. Alternatively, a sterile adhesive tab or disk 34 can be provided on the cap so that the disk can be removed, the sample inserted by passing a hypodermic needle through opening 22, puncturing membrane 30, and then, if desired, restoring the adhesive disk after the sample has been injected to maintain sterile integrity outside the vessel.

The vessel is then placed in a suitable conventional incubator, not shown and, the temperature of the vessel is brought to incubator temperature, e.g. 37°, if not already at that temperature. The vessel is then maintained at the temperature conditions previously suggested to foster the growth of the microorganisms contained in the vessel, if any. Microorganism growth will generate gas within the vessel, as is well known, causing the pressure within the vessel to increase and inelastically inflating the dome-like flaccid central portion 32 of the membrane, causing that portion to occupy substantially all of the interior of shell 16. From time to time, the vessel (and other like vessels in the incubator) will be checked for activity by very slowly pumping air into the incubator and noting the pressure of the incubator when each inflated central portion is caused to retract from its inflated condition. At that pressure, the incubator pressure will be equal to the pressure within the vessel. This can be done automatically, recording the time and pressure for each vessel.

Dome 16 and, optionally, all of cap 14, is preferably made of a transparent or at least translucent material. Membrane 30, or at least deformed portion 32, can be made of a material which is dark or reflective so as to be detectable when inflated by apparatus capable of sending light or the like through the transparent shell surrounding it. It is therefore possible to monitor the vessel from time to time to see if a sufficient change in pressure has occurred to indicate microorganism growth.

It is also possible to eliminate dome 16 entirely, allowing flaccid portion 32 to freely expand. Clearly, it could be easily seen or sensed and thus act as an indicator of gas generation within the vessel. However, it can also be overinflated and ruptured, especially if an elastic flaccid portion is used, creating a potentially dangerous condition and destroying the isolation between the vessel interior and the ambient. Accordingly, the use of dome 16 is greatly preferred.

The substantial increase in volume of portion 32 permits the use of very simple and inexpensive monitoring devices which allow the microorganism growth to be monitored automatically, permitting accurate determination of the rapidity of microorganism growth and activity, should that be significant to the particular microorganisms under consideration. In using the present invention it is likely that dozens or hundreds of vessels will be concurrently tested in a single incubator. It is also expected that the vessels would be incubated for days before microorganism growth is adequate to be sensed by a pressure increase. Accordingly, it is important to have an arrangement in which a tray of vessels can be inserted into an array of sensors for automatic polling.

Figure 3:
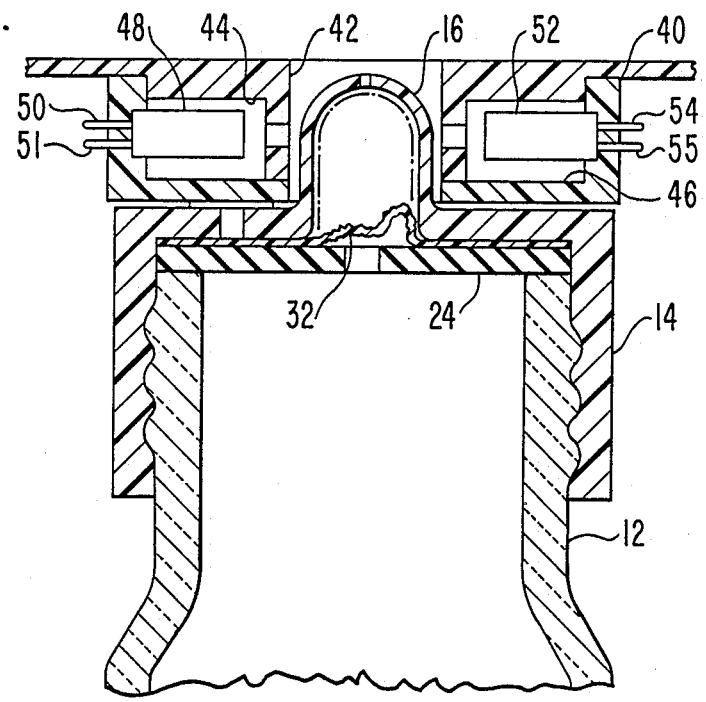
FIG. 3 is a partial side elevation similar to FIG. 2 and including pressure sensing means.
Figure 4:
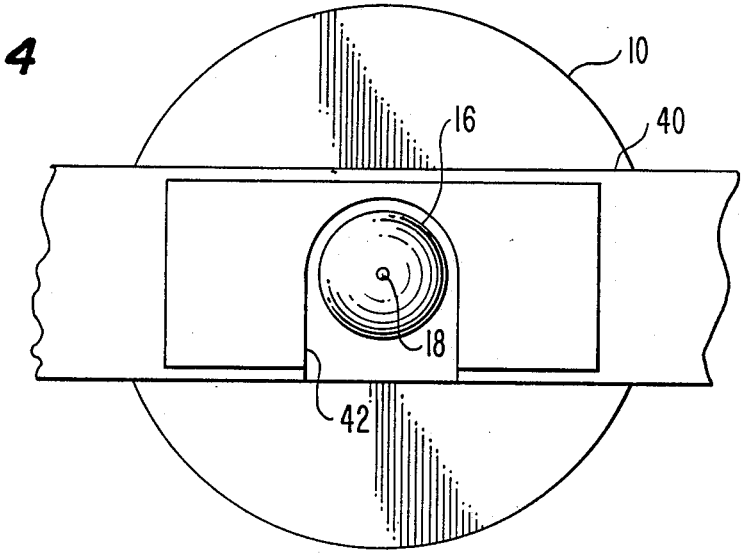
FIG. 4 is a top plan view of the apparatus of FIG. 3.

A suitable monitoring device is illustrated in FIGS. 3 and 4 in conjunction with the apparatus of FIG. 2 and includes a body 40 of a moldable, electrically non-conductive material. Body 40 is formed with a central slot 42 having a width greater than dome 16, the slot 42 extending entirely through the body. Recesses 44 and 46 are formed on opposite sides of the body, opening into slot 42. Recess 44 contains a photodetector device 48 having a photo-responsive surface directed toward dome 16, device 48 having electrodes 50 and 51 extending outwardly through body 40 for connection to suitable wires, not shown. In recess 46, a light source 52 is housed, body 40 having a suitable receptacle means 54 and 55 for receiving the electrodes of light source 42 and connecting those electrodes electrically to suitable wires which can be connected to a power source. Light source 52 is positioned so that light emanating therefrom can pass through dome 16. The dome is, of course, made transparent or translucent for this purpose.

Body 40 is arranged and dimensioned so that it can be supported above the upper surface of cap 14 with the light source and photodetector being positioned so that light from the source passes through the dome and is received by the detector when the flaccid indicator region is collapsed as illustrated in FIG. 3. When pressure within the vessel produced by gas generated by the microorganisms therein causes inelastic inflation of region 32, it expands into the light path between the source and photodetector, partially or totally occluding the light. The electrical output of photodetector 48 will be modified as a function of this reduced light, the direction of modification being dependent upon the type of photodetector selected. The change in light can be used to activate an alarm of some form or to produce a time record on a recording device to indicate when the generated gas reached a pressure level capable of causing the inflation.

As will be recognized, the outer surface of region 32 can be made reflective and the source and photodetector can be positioned adjacent each other so that light from the source reaches the photodetector only when the region 32 is sufficiently inflated so that a reflective surface thereof is presented in the path of the light from source 52.

Figure 5:
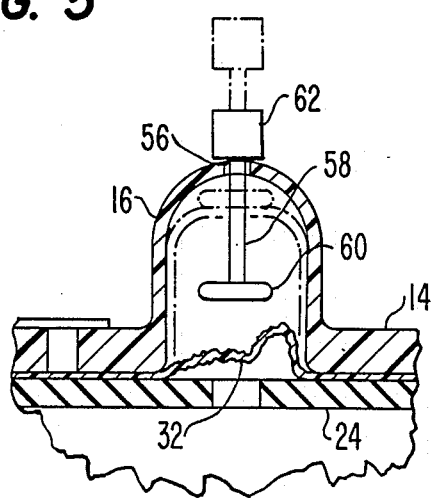
FIG. 5 is a partial side elevation, in section, of a further embodiment of an apparatus in accordance with the invention.

FIG. 5 shows a further embodiment of an apparatus in accordance with the invention in which a mechanical indicator is employed The apparatus is substantially identical to that shown in FIG. 2 except that the opening 56 at the top of dome 16 may be larger. An indicating plunger 58 passes through the opening and has an enlarged portion 60 at its lower end. An enlarged portion 62 is provided at the upper end, portion 60 being pushed upwardly by flaccid region 32 when it is inflated.

The embodiment of FIG. 5 has the disadvantage that flaccid portion 32 must lift the weight of the mechanical indicator including the plunger and its enlarged ends. However, it has the significant advantages that the indicator is visible when shell 16 is made of an opaque material. Additionally, enlarged portion 62 can be made to occlude light or reflect light, in a fashion similar to that discussed in connection with FIG. 3, with more definiteness since a sharp edge can be created to interfere with the light path. The plunger can, of course, be made of very light polymeric materials so that the force required to lift it is not significantly greater than that required to inflate the flaccid portion itself.

It is presently contemplated that the apparatus of the invention could be used with conventional bottles or vials supplied, as they are now, containing a culture medium for growing the microorganisms and with a rigid screw-on cap having a central hole and a rubber septum seal so that a patient's blood, drawn with a needle and syringe, could be inoculated into the bottle. The bottle would then be sent to the laboratory. The new cap structure, as shown in FIG. 2, would be supplied in an individual sterile package to keep at least the inside of liner 24 sterile. The laboratory technician would unscrew and discard the original cap and substitute the cap as shown in the Figures. The vessel with the new cap can then be incubated under conditions conducive to microorganism growth and monitored for gas production, as described above.

While certain advantageous embodiments have been chosen to illustrate the invention, it will be understood by those skilled in the art that various changes and modifications can be made therein without departing from the scope of the invention as defined in the appended claims.

What is claimed is:

1. A method of detecting activity of microorganism in a sample comprising the steps of providing a vessel having substantially rigid walls and having an opening into the interior of the vessel, providing a closure for closing the opening into the vessel, the closure including a membrane having a central region, deforming the central portion of the membrane to form a flaccid indicator region which is more movable by differences in pressure across the closure than the remainder of the membrane so that a difference in pressure causes the region to form a bulging dome, securely fastening the closure across the opening to seal the vessel;

placing a sample of the material to be tested in the vessel;

placing the vessel with closure and sample in an incubating chamber having a controllable temperature, and incubating the vessel in said incubating chamber for a selected interval of time at a temperature and pressure selected to promote microorganism activity within the vessel and consequent generation of gas, following said incubating changing the pressure within the incubating chamber until the dome assumes a substantially deflated state, measuring the incubation chamber pressure at which the dome is in said substantially deflated state, repeating the steps of changing and measuring the chamber pressure, and comparing the measured pressure with previous measured pressures to evaluate changes in pressure indicating microorganism activity.

2. A method according to claim 1 and further including providing a source of light directed toward the dome and a photodetector for receiving light from the source in the absence of a dome and to be occluded when a dome is formed and for producing a signal readable as an indication of greater pressure inside than outside of the vessel and measuring the resulting signal as a measure of microorganism activity.

* * * * *